United States Patent
Callas et al.

(10) Patent No.: US 6,811,546 B1
(45) Date of Patent: Nov. 2, 2004

(54) ENDOSCOPIC SURGICAL ACCESS PORT AND METHOD

(75) Inventors: Peter Callas, Redwood City, CA (US); John P. Lunsford, San Carlos, CA (US); Albert K. Chin, Palo Alto, CA (US); Michael Wei, San Mateo, CA (US)

(73) Assignee: Origin Medsystems, Inc., Santa Clara, CA (US)

( * ) Notice: Subject to any disclaimer, the term of this patent is extended or adjusted under 35 U.S.C. 154(b) by 364 days.

(21) Appl. No.: 09/648,660

(22) Filed: Aug. 25, 2000

(51) Int. Cl.[7] ............................................. A61M 5/178
(52) U.S. Cl. .................................................. 604/167.06
(58) Field of Search ................................ 606/190–194, 606/108, 1, 174, 185; 604/167.1–167.6, 174, 23–26, 167.01–167.04, 167.06

(56) References Cited

U.S. PATENT DOCUMENTS

| | | | |
|---|---|---|---|
| 4,424,833 A | 1/1984 | Spector et al. ............... 137/849 |
| 4,649,904 A * | 3/1987 | Krauter et al. ............... 600/154 |
| 4,653,477 A * | 3/1987 | Akui et al. .................. 600/154 |
| 4,685,447 A | 8/1987 | Iversen et al. ................. 128/1 |
| 4,809,679 A * | 3/1989 | Shimonaka et al. ......... 600/154 |
| 4,929,235 A | 5/1990 | Merry et al. ................. 604/167 |
| 5,073,169 A | 12/1991 | Raiken ........................ 604/180 |
| 5,104,383 A | 4/1992 | Shichman .................... 604/167 |
| 5,127,626 A | 7/1992 | Hilal et al. ............... 251/149.1 |
| 5,167,636 A | 12/1992 | Clement ...................... 604/167 |
| 5,197,955 A | 3/1993 | Stephens et al. ............. 604/167 |
| 5,226,891 A | 7/1993 | Bushatz et al. .............. 604/165 |
| 5,263,939 A | 11/1993 | Wortrich ..................... 604/174 |
| 5,330,437 A | 7/1994 | Durman ...................... 604/167 |
| 5,354,280 A | 10/1994 | Haber et al. ................ 604/167 |
| 5,366,446 A | 11/1994 | Tal et al. .................... 604/110 |
| 5,437,646 A * | 8/1995 | Hunt et al. ............. 604/167.04 |
| 5,496,345 A | 3/1996 | Kieturakis et al. ........... 606/192 |
| 5,607,397 A * | 3/1997 | Stephens et al. ........ 604/167.01 |
| 5,697,946 A * | 12/1997 | Hopper et al. ............... 606/185 |
| 5,725,553 A | 3/1998 | Moenning .................... 606/213 |
| 5,836,913 A | 11/1998 | Orth et al. ................... 604/107 |
| 5,855,549 A * | 1/1999 | Newman ...................... 600/135 |
| 5,868,773 A | 2/1999 | Danks et al. ................ 606/185 |
| 5,871,471 A | 2/1999 | Ryan et al. .................. 604/167 |
| 5,979,452 A * | 11/1999 | Fogarty et al. .............. 128/898 |
| 6,099,505 A | 8/2000 | Ryan et al. .................. 604/167 |
| 6,099,544 A | 8/2000 | Wolf et al. .................. 606/185 |
| 6,102,853 A | 8/2000 | Scirica et al. ............... 600/227 |
| 6,106,539 A | 8/2000 | Fortier ........................ 606/185 |
| 6,110,154 A | 8/2000 | Shimomura et al. ......... 604/256 |
| 6,129,713 A | 10/2000 | Mangosong et al. ......... 604/264 |
| 6,142,955 A | 11/2000 | Farascioni et al. ........... 600/562 |
| 6,146,400 A | 11/2000 | Hahnen ....................... 606/185 |
| 6,152,894 A | 11/2000 | Kubler ......................... 604/22 |
| 6,162,196 A | 12/2000 | Hart et al. ................... 604/167 |
| 6,162,236 A | 12/2000 | Osada ......................... 606/185 |

(List continued on next page.)

*Primary Examiner*—Kevin T. Truong
(74) *Attorney, Agent, or Firm*—Fenwick & West LLP

(57) ABSTRACT

A sliding gas-tight seal on an access port promotes insufflation of an anatomical space formed in tissue at a surgical site only during insertion of an endoscopic instrument through the access port into the anatomical space, and promotes deflation of the inflated space upon removal of the endoscopic instrument from within the access port. An inflatable balloon disposed about the port near the distal end may be selectively expanded to seal and anchor the access port within an incision through which a surgical procedure with insufflation is to be performed. Multiple resilient seals may be attached to the body of the port, and an auxiliary resilient seal may be inserted within the aperture of a seal attached to the body to accommodate a wide range of endoscopic instruments of various exterior dimensions inserted through the seals.

8 Claims, 2 Drawing Sheets

U.S. PATENT DOCUMENTS

| | | | |
|---|---|---|---|
| 6,165,124 A | * 12/2000 | Ouchi | 600/154 |
| 6,165,137 A | 12/2000 | Milliman et al. | 600/562 |
| 6,168,607 B1 | 1/2001 | Wattiez et al. | 606/185 |
| 6,187,002 B1 | 2/2001 | Long et al. | 606/46 |
| 6,189,533 B1 | 2/2001 | Simon et al. | 128/207.14 |
| 6,193,651 B1 | 2/2001 | DeFonzo | 600/201 |
| 6,197,041 B1 | 3/2001 | Shichman et al. | 606/185 |
| 6,200,263 B1 | 3/2001 | Person | 600/227 |
| 6,276,661 B1 | * 8/2001 | Laird | 251/61.1 |
| 6,599,237 B1 | * 7/2003 | Singh | 600/114 |
| 2001/0023332 A1 | * 9/2001 | Hahnen | 604/98.01 |

* cited by examiner

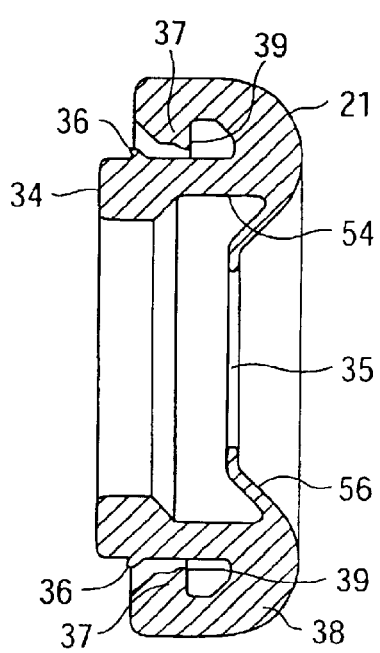
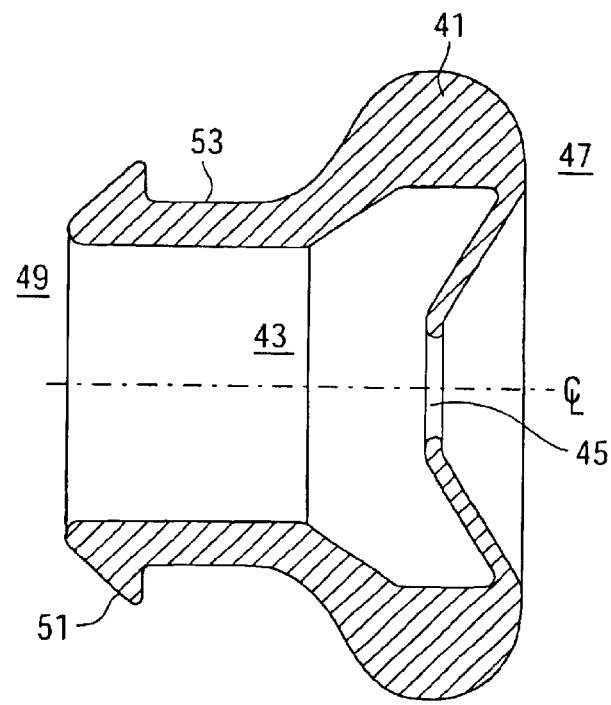
FIG. 5   FIG. 6
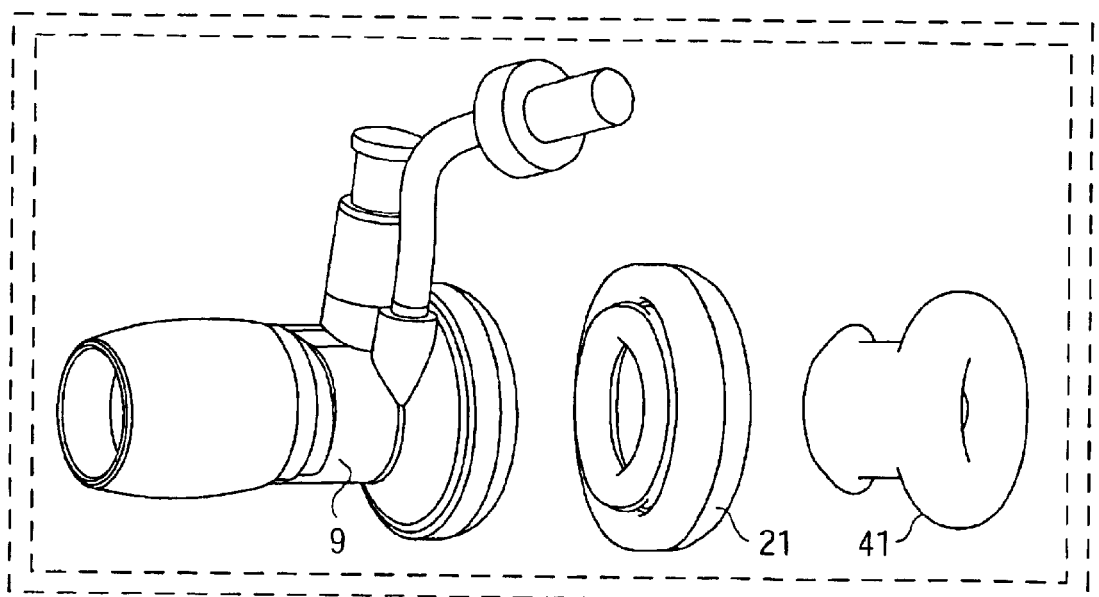
FIG. 7

ENDOSCOPIC SURGICAL ACCESS PORT AND METHOD

FIELD OF THE INVENTION

This invention relates to endoscopic surgical apparatus and methods of tissue dissection, and more particularly to a sliding gas seal for controlling insufflation of an endoscopic surgical site on a patient.

BACKGROUND OF THE INVENTION

Coronary bypass surgery commonly requires a length of the saphenous vein of the patient to form a shunting vessel around a site of stenosis or other blockage in a coronary artery. The saphenous vein was conventionally 'harvested' from the patient's leg through an incision extending the length of the section of saphenous vein to be harvested. Recently, endoscopic surgical procedures have replaced open-incision harvesting procedures and have significantly reduced patient trauma, discomfort, complication and recovery time. Specifically, contemporary vein-harvesting procedures require only a small incision over the saphenous vein to expose the vein, and then blunt tissue dissection is performed along the length of the vein using an elongated endoscopic cannula inserted through the incision to detach the vein and lateral branch vessels from connective tissue along the length of the vein to be harvested. The channel or anatomical space thus formed within the bluntly dissected tissue along the course of the vessel may be expanded to provide additional space within which to perform associated surgical procedures such as clipping and ligating lateral branch vessels using mechanical retractors inserted within the channel to elevate tissue away from the vein being harvested.

Alternatively, the channel or anatomical space formed along the course of the vessel may be retained in expanded condition by insufflating the channel with gas under pressure. The gas may be supplied through an access port which admits endoscopic instruments through a sliding gas-tight seal that is inserted into and sealed within the small initial incision over the saphenous vein. Conventional access ports commonly include a hollow body with an expandable peripheral balloon disposed about the outer distal end of the body, and with one or more diaphragm-type sliding seals disposed at the proximal end across the central bore of the hollow body. In operation, such conventional access port is inserted into a small incision and the peripheral balloon is then inflated to seal the port within the incision. Gas under pressure may then be supplied through the access port as elongated endoscopic instruments are inserted, and manipulated through the sliding seal during surgical procedures within the anatomical space formed along the vein, without significant loss of gas pressure within the anatomical space during insertions and removals of surgical instruments through the sliding seal of the access port. For convenience, the hollow body may include multiple sliding gas seals that are selectively positioned on the proximal end of the port to accommodate a selection of elongated instruments of different diameters passing through the central bore of the hollow body. Such access ports include a flapper valve to inhibit outflow of gas there through as an elongated instrument is withdrawn from the central bore. However, the versatility of selectable seals and flapper valves to accommodate endoscopic instruments of various diameters significantly extends the length of the hollow body and requires additional manual re-configuration to position a selected seal over the proximal end of the hollow body to provide a sliding seal of appropriate dimensions to accommodate the diameter of a selected endoscopic instrument.

SUMMARY OF THE INVENTION

In accordance with embodiments of the apparatus and method of the present invention, an access port is provided which obviates the need for flapper valves and selectable sliding seals that snap toggle into position over the proximal end of the hollow body. This facilitates insufflation of an anatomical space during the interval while an endoscopic instrument is positioned through the hollow body. In recognition of the typically small spatial volume of a channel or anatomical space formed along the saphenous vein, it has been discovered that insufflation need only be established during insertion and manipulation of an endoscopic instrument through the access port, and that re-pressurization of the small volume can be satisfactorily restored within a very brief interval following insertion of an endoscopic instrument through the sliding seal of the access port.

BRIEF DESCRIPTION OF THE DRAWINGS

FIG. 5 is a sectional view of one sliding gas seal for engagement on the proximal end of the body of FIG. 3;

FIG. 6 is a sectional view of a sliding gas seal for assembly on the embodiment of FIG. 1; and FIG. 7 is a perspective view of an access port kit according to the present invention.

DETAILED DESCRIPTION OF THE INVENTION

Figure 1:
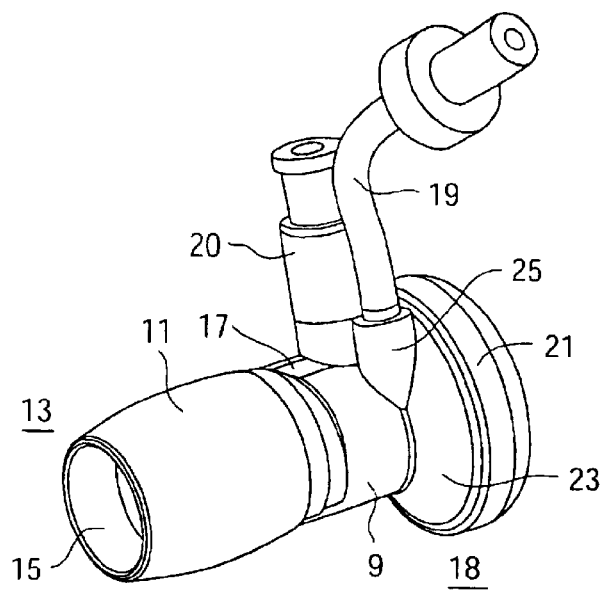
FIG. 1 is perspective view of an access port in accordance with one embodiment of the present invention.
Figure 2:
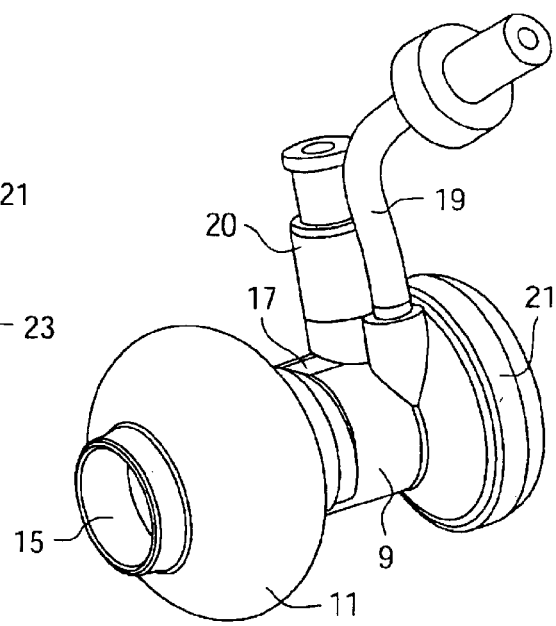
FIG. 2 is a perspective view of the access port of FIG. 1 with the incision-sealing balloon inflated.

Referring now to FIG. 1, there is shown a perspective view of the access port according to one embodiment of the present invention in which the hollow body 9 of fluid-impervious material includes a central bore 15 and a generally toroidally-shaped balloon 11 disposed about the outer periphery of the body 9 near the distal end 13 thereof. The interior diameter of the central bore 15 through the hollow body 9 is sized to accommodate the largest diameter of endoscopic instrument therein and may be about 0.6" at the distal end 13, and may flair out to a wider diameter of about 0.9" at the proximal end 18. A fluid or air passage 17 along an outer wall of the body 9 connects to an external fluid-tight coupling or fitting 20 for coupling to a source of gas under pressure, such as a syringe, in order to selectively inflate the balloon 11 within the confines of an initial cutaneous incision near a saphenous vein that is to be harvested. Inflating the balloon 11 with fluid under pressure, as shown in FIG. 2, seals and mechanically anchors the body 9 within an incision to serve as the access port for endoscopic instruments thereafter inserted through the central bore 15 of the hollow body 9 into the incision.

Figure 3:
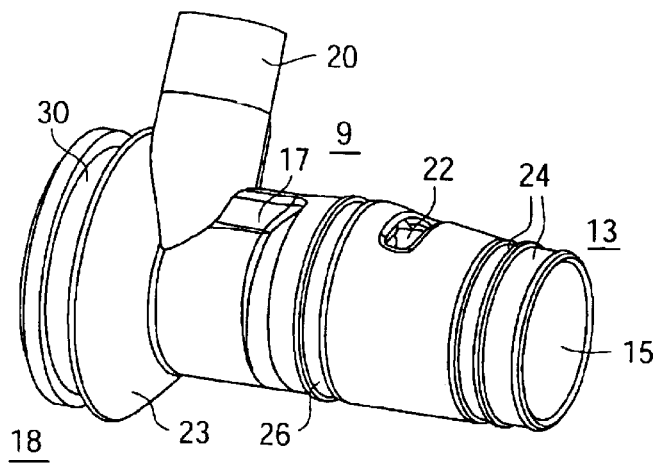
FIG. 3 is a perspective view of the body of the access port of FIG. 1 as a molded component.

Referring now to FIG. 3, there is shown a perspective view of the body 9 as a molded component formed, for example, of bioinert material such as polycarbonate. Specifically, the body 9 includes an integral air passage 17 communicating with the gas fitting 20 and the aperture 22 (within the volume confined by the balloon 11, not shown).

This integral air passage thus facilitate selective inflation of the balloon 11 via a fitting 20. Alternatively, the fitting 20 may include a one-way valve to retain inflation of the balloon until such valve is selectively released. The balloon 11 is attached to the body 9 within the circumferential groove, or grooves, 24 near the outer perimeter of the distal end 13, and is also attached to the circumferential groove 26 about the outer perimeter of the body 9 at a location thereon intermediate the distal end 13 and proximal end 18. The integral air passage 17 extends the outer dimension of the body 9 between the fitting 20 and the aperture 22, so groove 26 may be elliptical in the plane normal to the axis of the central bore 15. A balloon 11 thus attached to the body 9, as described above, may inflate in substantially toroidal configuration, as illustrated in FIG. 2, with an elliptical shape disposed within groove 26 and a substantially circular shape disposed within groove 24.

Figure 4:
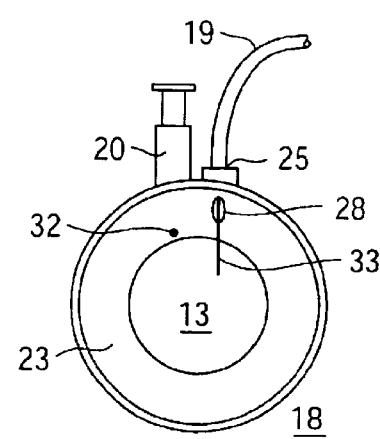
FIG. 4 is a proximal end view of the body of FIG. 3.

At the proximal end 18 of the body 9, the central bore 15 flairs out to a larger diameter over a short transition section 23 that provides an internal wall which tapers between the larger and smaller diameter segments of the central bore 15. The outer perimeter of the proximal end 18 of the body 9 includes a recessed groove 30 that accommodates gas-tight attachment of a resilient seal, later described herein. The expanded diameter of the central bore 15 near the proximal end 18 of the body 9 accommodates a wide range of angulation of an endoscopic instrument within the central bore 15 without interference from the side walls of the internal bore. Also, as shown in the proximal end view of FIG. 4, an insufflation gas inlet 25 is formed on the transition section 23, with an internal aperture 28 positioned in the tapering internal wall of the transition section 23. This assures that insufflating gas or other fluid supplied through the conduit 19 and the aperture 28 will not be blocked or restricted by an endoscopic instrument of largest diameter inserted within the central bore 15. In another embodiment of the present invention, the conduit 19 for insufflating gas or other fluid under pressure may be normally sealed off, for example, via a resiliently-biased disk against a downstream valve seat, with a control arm 33 rigidly attached centrally on the disk and protruding through the aperture 28 into the central bore 15 to open the valve in response to an endoscopic instrument inserted in central bore 15 to displace the control arm 33. Molding of the body 9 with an air passage between the fitting 20 and the aperture 22 (for inflating the balloon 11) is greatly facilitated by a pin-like mandrel disposed away from, but aligned with, the central bore 15 and emanating through the internal tapered wall of the transition section 23. Such pin-like mandrel intersects with another mandrel that forms the internal bore through the fitting 20 to provide the integrally-molded air passage 17 between fitting 20 and aperture 22, with a remnant aperture 32 remaining in the internal tapered wall where the pin-like molding mandrel was withdrawn. This aperture 32 may be permanently plugged with a drop of glue or sealant, or the like, to provide a gas-tight air passage between fitting 20 and the aperture 22. Alternatively, a tube as an insert may be molded into the body 9 to form the air passage between fitting 20 and aperture 22, without an aperture 32 formed during such molding procedure.

In another embodiment, the body 9 and a sliding seal 21 may be integrally formed as a single molding of a bioinert material such as silicone rubber. In such embodiment, the more rigid section of the body 9 includes thicker walls and the more flexible section of the seal 21 includes thinner walls, with other components, features and configuration (except a grove 30) formed as previously described herein.

Referring now to FIG. 5, there is shown a sectional view of a generally round seal 21 for gas-tight attachment to the generally cylindrical proximal end 18 of the body 9. The seal 21 is formed of resilient, flexible polymeric material to include a central aperture 35. The aperture 35 overlays and aligns with the central bore 15 at the proximal end of the hollow body. The aperture 35 has a smaller diameter than the largest endoscopic instrument to be inserted through the hollow body 9. A sliding gas-tight seal is thus formed about the outer generally cylindrical surface of an endoscopic instrument during insertion thereof through the hollow body 9. The outer perimeter of the seal 21 is configured to overlap the proximal end 18 of the body 9 and resiliently snap into groove 30 for gas-tight and mechanically-secure attachment to the body 9. Specifically, the distal end 34 is configured to insert within the internal walls of the proximal end 18 of the body 9, and includes an integrally-formed raised or protruding ring 36 on such outer diameter to provide a deformable gas-tight seal between the seal 21 and the internal walls of the body 9. In addition, the overlapping flange 38 at the proximal end of the seal 21 includes a descending and inwardly extending portion 37 that is integrally formed on the seal 21 to engage within the groove 30 in the outer perimeter near the proximal end of the body 9. In addition, the inwardly extending portion includes an integrally-formed inwardly extending or intruding ring 39 that provides a deformable gas seal within the groove 30 in body 9. The seal 21 thus configured forms gas-tight seals about the proximal end 18 of the body 9, and forms a sliding gas-tight seal about an endoscopic instrument inserted through the aperture 35. The aperture 28 into the hollow body 9 is positioned interior of seal 21 for supplying gas under pressure via conduit 19 to an anatomical space into which the access port is inserted. Thus, with the body 9 sealed and anchored within an incision by the inflated balloon 11, and with an endoscopic instrument inserted through the seal 21 and hollow body 9, an anatomical space of confined volume is formed about a saphenous vein to be harvested which can be insufflated with gas under pressure supplied to the confined volume through the conduit 19 and aperture 28. As the endoscopic instrument is removed from the access port, the fluid seal around the endoscopic is disabled, and air or other fluid under pressure within the confined volume about the saphenous vein equalizes rapidly toward ambient pressure. Only after an endoscopic instrument is again inserted within the central bore of the hollow body 9 is the fluid seal re-formed at aperture 35, and the confined volume about the saphenous vein re-insufflated with gas or other fluid under pressure that may be continuously supplied via the aperture 28.

For operation with an endoscopic instrument of smaller exterior diameter than would form a seal within aperture 35, sliding auxiliary gas seal 41 may be formed in the configuration as illustrated in FIG. 6 for insertion into the aperture 35 of seal 21. The auxiliary seal 41 is substantially circularly toroidal with an internal bore 43 of larger diameter than the diameter of the sealing aperture 45 at the proximal end 47. A tapered and outwardly extending hook-like ring 51 is integrally formed on the distal end 49 of the auxiliary seal 41 at a distance from the proximal end 47 suitable for engaging the inner surface 54 behind the diaphragm member 56. Alternatively, the ring 51 may be integrally formed on the distal end 49 of the auxiliary seal 41 at a distance from the proximal end 47 suitable for engaging the distal end 34 of the seal 21. The outer diameter 53 is disposed to fit within the inner diameter of seal 21 at the distal end thereof. In this way, the auxiliary seal 41 may form a gas-tight and mechanically-stable auxiliary seal about endoscopic instruments of smaller diameter suitable for forming a sliding seal within aperture 45. The toroidally-shaped seal 21, and auxiliary seal 41 may be formed of a flexible, resilient material such as polyurethane, silicone, latex rubber, Nitrile, or the like, to exhibit resilient flexibility upon installation of seal 21 over the proximal end 18 of the body 9, and upon optional installation of the auxiliary seal 41 within the aperture 35 of seal 21. A seal 21 formed and assembled in this manner on the body 9 with optional auxiliary seal 41 inserted in seal 21, significantly reduces the length and mass and associated cost of an access port suitable for accommodating large-diameter and small-diameter endoscopic instruments while also supporting insufflation of a surgical site, such as along a saphenous vein, of relatively small confined volume. In addition, the short length of body 9 greatly extends the range of angulation of an endoscopic instrument within the central bore 15 without adversely altering the position of the body 9 sealed within an incision. And, the inner walls of the seal 21 and auxiliary seal 41 serve as bumpers to limit angular and lateral movement of an endoscopic instrument and prevent distortion of the associated aperture in response to excessive angular movement. The fitting or coupling 20 and the conduit 19 and insufflation gas, inlet 25 may also be oriented in substantial axial alignment, rather than in lateral alignment, with the central bore 15 to increase the range of angular orientations of the body 9 within an incision. Axial configuration of the gas ports in another embodiment of the present invention facilitates reduced size of the body and insertion thereof into an incision with the seal 21 oriented distally and the balloon 11 oriented proximally. And, an eccentric mounting of the balloon on the body at a location thereon intermediate the distal and proximate ends promotes wider angles of orientation of the central bore relative to an incision formed above a saphenous vein to be harvested. The body with attached balloon and one or more resilient seals having apertures of various diameters, and including an auxiliary seal 41 for fluid-tight insertion into the aperture of a seal 21 that attaches to the proximal end of the body 9, may all be assembled in pre-sterilized condition within a hermetically-sealed conventional tray pack or pillow pack, as illustrated in FIG. 7, to facilitate forming an insufflation access port with sliding seals about endoscopic instruments of various exterior dimensions.

What is claimed is:

1. A body for an access port for insufflating a surgical site, comprising:
    the body including a central bore therethrough from a distal end to a proximal end thereof and including on an outer wall thereof near the distal end an attachment site for an inflatable balloon;
    a fluid passage within a wall of the body communicating with the attachment site and with a fluid inlet to form a fluid channel for selectively inflating a balloon at the attachment site with fluid under pressure supplied to the inlet;
    the body including near the proximal end thereof an attachment rim for receiving thereat a resilient sealing member to form a fluid-tight seal with the body and with an aperture therein substantially aligned with central bore; and
    the body including an insufflation inlet disposed intermediate the distal and proximal ends in communication with the central bore.

2. The body of an access port according to claim 1 including a section intermediate the proximal and distal ends for transitioning from the central bore near the distal end to a larger internal bore near the proximal end.

3. The body of an access port according to claim 2 in which the insufflation inlet communicates with the central bore and larger internal bore within the transition section.

4. The body of an access port according to claim 2 in which the fluid inlet is disposed proximate the transition section of the body and near the insufflation inlet.

5. The body of an access port according to claim 1 in which the attachment rim includes a recessed groove within an outer wall of the body near the proximal end thereof for receiving a resilient sealing member therein in fluid-tight seal with the body.

6. A sealing member for an insufflation access port having a body with a central bore therethrough between distal and proximal ends thereof, the sealing member for attachment to the proximal end of the body, comprising:
    a hollow cylinder of resilient material having a distal end dimensioned to insert within the central bore of the body at the proximal end thereof and including an outwardly extending flange integrally formed on the proximal end of the cylinder to overlay the proximal end of the body, the flange including an aperture therethrough in position to substantially align with the central bore of the body upon attachment thereto for receiving therein an endoscopic instrument in fluid-tight sliding sealing engagement within the aperture; and
    a protruding ring integrally formed about the cylinder near the distal end thereof for deforming within the central bore of the body to form a fluid-tight seal therewith.

7. The sealing member according to claim 6 for attachment to the body of an access port having a recessed groove about the periphery of the body near the proximal end thereof, the flange of the sealing member comprising:
    a substantially cylindrical section extending substantially concentrically with the hollow cylinder toward the distal end thereof to overlay the proximal end of the body and terminate with an inwardly intruding rim integrally formed with the cylinder section and the flange and the hollow cylinder, said rim being dimensioned and positioned to engage the recessed groove about the periphery of the body in fluid-tight sealing engagement therein; and
    an intruding ring integrally formed on said intruding rim for deforming within the recessed groove to form a fluid-tight seal therein.

8. An auxiliary sealing member for insertion within the aperture of the sealing member of claim 6, comprising:
    a hollow cylinder of resilient material including an end segment integrally formed on a proximal end of the cylinder having an aperture therethrough, and having an outwardly protruding flange integrally formed about a distal end thereof, the hollow cylinder of the auxiliary sealing member being dimensioned to form a fluid-tight seal within the aperture of the sealing member, and the protruding flange on the distal end of the auxiliary sealing member being disposed to engage the distal end of the sealing member for retaining the auxiliary sealing member within the aperture of the sealing member.

* * * * *